(12) United States Patent
Kawabata et al.

(10) Patent No.: US 11,422,071 B2
(45) Date of Patent: Aug. 23, 2022

(54) SUBSTRATE ANALYSIS METHOD AND SUBSTRATE ANALYZER

(71) Applicant: IAS, INC., Tokyo (JP)

(72) Inventors: Katsuhiko Kawabata, Tokyo (JP); Sungjae Lee, Tokyo (JP); Takuma Hayashi, Tokyo (JP)

(73) Assignee: IAS, INC., Tokyo (JP)

( * ) Notice: Subject to any disclaimer, the term of this patent is extended or adjusted under 35 U.S.C. 154(b) by 0 days.

(21) Appl. No.: 17/415,191

(22) PCT Filed: Nov. 6, 2019

(86) PCT No.: PCT/JP2019/043353
§ 371 (c)(1),
(2) Date: Jun. 17, 2021

(87) PCT Pub. No.: WO2020/137173
PCT Pub. Date: Jul. 2, 2020

(65) Prior Publication Data
US 2022/0042882 A1 Feb. 10, 2022

(30) Foreign Application Priority Data

Dec. 26, 2018 (JP) .............................. JP2018-242929

(51) Int. Cl.
*G01N 1/28* (2006.01)
*G01N 19/08* (2006.01)
*G01N 1/10* (2006.01)

(52) U.S. Cl.
CPC ............... *G01N 1/28* (2013.01); *G01N 19/08* (2013.01); *G01N 2001/1006* (2013.01)

(58) Field of Classification Search
CPC .. G01N 1/28; G01N 19/08; G01N 2001/1006; G01N 2033/0095;
(Continued)

(56) References Cited

U.S. PATENT DOCUMENTS 10,688,485 B2 * 6/2020 Kawabata ................. B01L 3/02
2002/0153482 A1 10/2002 Lin
(Continued)

FOREIGN PATENT DOCUMENTS

JP     H 10-092784 A    4/1998
JP     2002134576 A     5/2002
(Continued)

*Primary Examiner* — Nimeshkumar D Patel
*Assistant Examiner* — Nashmiya S Fayyaz
(74) *Attorney, Agent, or Firm* — Roberts & Roberts, LLP

(57) ABSTRACT

A substrate analysis method using a nozzle for substrate analysis which discharges an analysis liquid from a tip thereof, scans a substrate surface with a discharged analysis liquid, and sucks the analysis liquid. This is done by arranging a liquid catch plate that catches the discharged analysis liquid, thus retaining analysis liquid discharged between the nozzle tip and the liquid catch plate; positioning the substrate so that the end part thereof can be inserted between the nozzle tip and the liquid catch plate; bringing the end part of the substrate into contact with analysis liquid retained between the nozzle tip and liquid catch plate; and moving the nozzle and liquid catch plate concurrently along a periphery of the substrate, while keeping the end part of the substrate in contact with the analysis liquid, to analyze the end part of the substrate.

3 Claims, 3 Drawing Sheets

(58) Field of Classification Search
CPC .............. G01N 33/00; G01N 35/1009; G01N 2001/2826; G01N 27/62
USPC ........................................................ 73/865.8
See application file for complete search history.

(56) References Cited

U.S. PATENT DOCUMENTS

| | | | | |
|---|---|---|---|---|
| 2009/0309905 A1* | 12/2009 | Yoshioka | .............. | G02F 1/1303 |
| | | | | 347/8 |
| 2018/0217036 A1* | 8/2018 | Kawabata | ................ | G01N 1/28 |
| 2019/0358622 A1* | 11/2019 | Kawabata | ................ | B01L 3/02 |
| 2020/0003701 A1* | 1/2020 | Liao | ................ | G01N 21/95607 |

FOREIGN PATENT DOCUMENTS

| | | | | |
|---|---|---|---|---|
| JP | 2005109292 | | 4/2005 | |
| JP | 200601234 A | | 1/2006 | |
| JP | 2006013234 A | | 1/2006 | |
| JP | 2006041504 | | 2/2006 | |
| JP | 2008159657 | | 7/2008 | |
| JP | 4521861 | | 8/2010 | |
| JP | 2011128033 | | 6/2011 | |
| JP | 2012074717 A | | 4/2012 | |
| JP | 2014017280 | | 1/2014 | |
| JP | 2014514743 A | | 6/2014 | |
| JP | 2017020992 | | 1/2017 | |
| JP | 2017156338 A | * | 9/2017 | ......... H01L 21/6708 |
| WO | 2017149833 | | 9/2017 | |
| WO | 2019016847 | | 1/2019 | |
| WO | WO-2019016847 A1 | * | 1/2019 | ............... G01N 1/02 |

* cited by examiner

SUBSTRATE ANALYSIS METHOD AND SUBSTRATE ANALYZER

CROSS REFERENCE TO RELATED APPLICATIONS

The present application is a U.S. National Phase entry of International Appln. No. PCT/JP2019/043353 filed on Nov. 6, 2019, which claims convention priority from Japanese Patent Application No. P2018-242929 filed on Dec. 26, 2018, now Japanese Patent No. P6675652 registered on Mar. 13, 2020, all of which are incorporated herein by reference.

TECHNICAL FIELD

The present invention relates to a method and a substrate analyzer, used for analyzing an object to be analyzed such as trace metal contained in the substrate.

BACKGROUND ART

Substrate such as semiconductor wafer has been analyzed by detecting metal, organic substance and so forth that contaminate the substrate typically in the process of manufacture, by use of a trace amount of analysis liquid. For example, when a substrate in which a silicon oxide film or nitride film is formed on a base such as silicon wafer is analyzed, a typical procedure is such as etching off the formed film typically by vapor phase decomposition as a pre-treatment, discharging a micro volume of analysis liquid from a tip of a nozzle, scanning a substrate surface with the discharged analysis liquid so as to incorporate any metal or organic substance which are the subject to be analyzed, and then by analyzing the analysis liquid by inductively-coupled plasma mass spectrometry (ICP-MS).

Now, the substrate such as semiconductor wafer, when handled for conveyance or loading, has been housed in a housing cassette in order to avoid as possible any failure such as contamination, in which an outer circumferential edge of the substrate is inevitably brought into contact with the housing cassette. The substrate, with its edge thus brought into contact with the housing cassette, is predicted to be polluted at the edge, and the pollution at the edge is anticipated to diffuse over the substrate surface. Hence, a practice, having been employed for the substrate such as semiconductor wafer, is to analyze not only the sursubstrate surface, but also the edge of the substrate.

Detail of the edge of the substrate will be described with respect to FIG. 1. FIG. 1 illustrates a part of a cross-section of a substrate W such as semiconductor wafer. The substrate W such as semiconductor wafer is processed at the outer circumferential edge by so-called beveling (a process for chamfering the outer circumference or the like of a substrate). In the present application as illustrated in FIG. 1, an area that covers a chamfered part 1 and an outermost edge 2 (a region indicated by arrow B in FIG. 1) will be referred to as a "bevel part"; whereas a range that covers a boundary region between the chamfered part 1 of the bevel part B and a top face 3 of the substrate, and a boundary region between the chamfered part 1 of the bevel part and a back face 4 of the substrate (a region indicated by arrow E in FIG. 1) will be referred to as an "edge part".

Methods for analyzing the edge of such substrate are described typically in Patent Document 1 and Patent Document 2. Patent Document 1 proposes a method for collecting a chemical liquid on a semiconductor wafer, which is devised to keep the chemical liquid (analysis liquid) in contact with a surface of a semiconductor wafer, to scan the chemical liquid in a circumferential direction, and to collect an impurity-containing chemical liquid, the method includes: a first step of collecting the impurity-containing chemical liquid by scanning in the circumferential direction, while positioning a radial position of the chemical liquid at a position in a top flat face part of the semiconductor wafer where the chemical liquid can contact with the a boundary region adjoining to the chamfered part; and a second step of collecting the impurity-containing chemical liquid by scanning in the circumferential direction, while positioning a radial position of the chemical liquid at a position where the chemical liquid can contact with both of the semiconductor wafer and the boundary region of the chamfered part.

Patent Document 2 proposes an analysis method by use of a substrate processing apparatus, the apparatus includes: a collection jig that has a cylindrical component having an inner space capable of retaining a liquid droplet, and a throughhole through which the inner space can communicate with an opening positioned at the lower end, and having an axial center in a vertical direction; and a transfer mechanism capable of relatively moving the collection jig over a face of a substrate, while keeping the liquid droplet exposed from the inner space in contact with the substrate, in which a size of the opening is adjusted so that a predetermined amount of the liquid droplet reserved in the inner space can sag from the opening without falling, when the collection jig is supported in the air.

RELATED ART DOCUMENT

Patent Documents

Patent Document 1: JP 4521861 B2
Patent Document 2: JP 2008-159657 A

The analytical method described in Patent Document 1 can analyze the chamfered part on the top flat face side of the semiconductor wafer, but can analyze neither the chamfered part on a back flat face side of the semiconductor wafer, nor a boundary region adjoining to the chamfered part (on the back flat face side of the semiconductor wafer). The method also needs the steps to be carried out twice, possibly making it more difficult to speed up the analysis. Meanwhile, Patent Document 2 can analyze the bevel part B and the edge part E illustrated in FIG. 1 of the present application, but needs a specially shaped collection jig. Such specially-shaped collection jig, when used for the analysis, would be difficult to be cleaned up due to its special shape, in which insufficient cleaning tends to cause residual memory, and is worried to adversely affect accuracy of the analysis. In addition, feeding and collection of the analysis liquid through the collection jig needs an additional jig besides the collection jig, making the analysis labor-consuming.

SUMMARY OF THE INVENTION

Problems to be Solved by the Invention

It is therefore an object of the present invention to provide an analytical technique that enables simpler and speedier analysis of an end part (bevel part, edge part) of a substrate illustrated in FIG. 1 of the present application, by use of an analysis method of a substrate by which an analysis liquid is discharged from a tip of a nozzle, the substrate is scanned with the thus discharged analysis liquid, and then the analysis liquid is analyzed.

Means for Solving the Problems

The present invention provides an analysis method of a substrate by use of a nozzle for substrate analysis which discharges an analysis liquid from a tip, scans a substrate surface with a discharged analysis liquid, and then sucks the analysis liquid to analyze an end part of the substrate. The method includes the steps of: arranging a liquid catch plate, which catches the discharged analysis liquid, at a position opposite to a nozzle tip to thereby retain the analysis liquid discharged from the tip between the nozzle tip and the liquid catch plate; positioning the substrate so that the end part thereof can be inserted between the nozzle tip and the liquid catch plate; bringing the end part of the substrate into contact with the analysis liquid retained between the nozzle tip and the liquid catch plate; and moving the nozzle and the liquid catch plate concurrently along a periphery of the substrate, while keeping the end part of the substrate in contact with the analysis liquid.

The present invention is readily applicable to an existing apparatus simply by adding the liquid catch plate, and enables simple and speedy analysis only by concurrently moving the nozzle and the liquid catch plate, while keeping the end part of the substrate in contact with the analysis liquid retained between the nozzle tip and the liquid catch plate. Washing the liquid catch plate with ultrapure water can easily suppress residual memory, and can keep a high level of accuracy of analysis. The analysis method of the present invention also enables analysis only within the bevel part B or over the edge part E illustrated in FIG. 1, by controlling a mode of contact of the end part of the substrate, when brought into contact with the analysis liquid retained between the nozzle tip and the liquid catch plate. Note that "scans a substrate surface" in the present invention means an operation of moving the analysis liquid discharged from the nozzle tip, on the substrate surface, and typically means to cause relative movement of the substrate surface and the nozzle, by moving the nozzle from inside toward the outside, while rotating the substrate (wafer W).

In the analysis method of a substrate of the present invention, a technique for concurrently moving the nozzle and the liquid catch plate along the periphery of the substrate may be such as synchronously moving the nozzle and the liquid catch plate, or such as moving or rotating the substrate, while keeping the nozzle and the liquid catch plate stationary. In short, the analysis liquid to be brought into contact with the end part of the substrate may only move relative to the end part of the substrate. In an exemplary case where an end part of an orientation flat formed in a semiconductor wafer is to be analyzed, a necessary operation may only be such as bringing the analysis liquid into contact with the end part of the substrate where the orientation flat is formed, and moving the analysis liquid along the orientation flat.

The liquid catch plate in the present invention is preferably hydrophobic. This is because the analysis liquid discharged from the nozzle tip can be retained reliably between the nozzle tip and the liquid catch plate, with the aid of surface tension of the analysis liquid. The liquid catch plate in the present invention is preferably made of a hydrophobic material, such as polytetrafluoroethylene (PTFE) for example.

The nozzle, used in the analysis method of a substrate according to the present invention, is preferably constituted by a triple concentric tube that includes a tube through which the analysis liquid is discharged and sucked; a first outer tube arranged around an outer circumference of the tube so as to surround the analysis liquid dragged for scanning; and a second outer tube arranged around an outer circumference of the first outer tube. The nozzle further preferably includes a first exhaust unit having an exhaust path arranged between the tube and the first outer tube; and a second exhaust unit having an exhaust path arranged between the first outer tube and the second outer tube. With a nozzle having such triple concentric tube structure, the analysis liquid discharged from the tip of the tube can be retained reliably between the nozzle tip and the liquid catch plate, when the exhaust path between the tube and the first outer tube, and the exhaust path between the first outer tube and the second outer tube, are controlled under a depressurized atmosphere, respectively by use of the first exhaust unit and the second exhaust unit.

The nozzle, applicable to the analysis method of a substrate according to the present invention, may be constituted by a dual concentric tube that includes a nozzle body through which the analysis liquid is discharged and sucked; and an outer tube arranged around an outer circumference of the nozzle body so as to surround the analysis liquid dragged for scanning. The nozzle may further include an exhaust unit having an exhaust path arranged between the nozzle body and the outer tube. Since the nozzle having such dual concentric tube structure is composed of the nozzle body and the outer tube, so that the analysis liquid discharged from the nozzle body tip can be retained reliably between the nozzle tip and the liquid catch plate, when a space formed between the nozzle body and the outer tube is controlled under a depressurized atmosphere.

The analysis method of a substrate of the present invention may be practiced by use of a substrate analyzer that includes a nozzle for substrate analysis which discharges an analysis liquid from a tip, scans a substrate surface with a discharged analysis liquid, and then sucks the analysis liquid, the substrate analyzer includes: a nozzle for substrate analysis, which is constituted by a triple concentric tube that includes a tube through which the analysis liquid is discharged and sucked, a first outer tube arranged around an outer circumference of the tube so as to surround the analysis liquid dragged for scanning, and a second outer tube arranged around an outer circumference of the first outer tube. The nozzle further includes a first exhaust unit having an exhaust path arranged between the tube and the first outer tube, and a second exhaust unit having an exhaust path arranged between the first outer tube and the second outer tube; a liquid catch plate control unit that arranges, opposite to the nozzle tip, a liquid catch plate that catches the analysis liquid discharged through the tube; and a drive unit capable of synchronously moving the nozzle and the liquid catch plate relative to the substrate.

The nozzle in the substrate analyzer of the present invention, when in the form of triple concentric tube, may have any size of the individual parts without particular limitation. The nozzle for substrate analysis may be prepared while properly adjusting the size depending on type and size of the substrate to be analyzed, and analytical conditions. Dimensions applied at present include ⅛ inches for the inner diameter of the tube (0.2 mm to 0.5 mm in thickness of the tube), 8 mm for the inner diameter of the first outer tube (1 mm to 2 mm in thickness of the first outer tube), and 18 mm for the inner diameter of the second outer tube (1 mm to 2 mm in thickness of the second outer tube).

The liquid catch plate in the substrate analyzer of the present invention may have any shape without particular limitation, and preferably has a shape of short column, on the circular face of which the analysis liquid may be caught.

It is preferable to properly process, in advance, the circular face of the liquid catch plate, on which the analysis liquid is caught, so as to have a diameter matched to the diameter of the first outer tube or the diameter of the second outer tube of the triple concentric tube-type nozzle. For example, for a triple concentric tube-type nozzle with a 20-mm second outer tube (18 mm in inner diameter, 22 mm in outer diameter), a 10-mm first outer tube (8 mm in inner diameter, 12 mm in outer diameter), and a ⅛-inch tube, the circular face of the liquid catch plate, on which the analysis liquid is caught, may have a diameter of 8 to 12 mm.

The analysis method of a substrate of the present invention may alternatively be practiced by use of a substrate analyzer that includes a nozzle for substrate analysis which discharges an analysis liquid from a tip, scans a substrate surface with a discharged analysis liquid, and then sucks the analysis liquid, the substrate analyzer includes: a nozzle for substrate analysis, which is constituted by a dual concentric tube that includes a nozzle body through which the analysis liquid is discharged and sucked, and an outer tube arranged around an outer circumference of the nozzle body so as to surround the analysis liquid dragged for scanning. The nozzle further includes an exhaust unit having an exhaust path arranged between the nozzle body and the outer tube; a liquid catch plate control unit that arranges, opposite to the nozzle tip, a liquid catch plate that catches the analysis liquid discharged through the nozzle body; and a drive unit capable of synchronously moving the nozzle and the liquid catch plate relative to the substrate.

The nozzle in the substrate analyzer of the present invention, when in the form of dual concentric tube, may have any size of the individual parts without particular limitation. The nozzle for substrate analysis may be prepared while properly adjusting the size depending on type and size of the substrate to be analyzed, and analytical conditions. At present, employed are the nozzle body with an inner diameter of 8 mm (with a thickness of 1 mm to 2 mm), and the outer tube with an inner diameter of 18 mm (with a thickness of 1 mm to 2 mm), where the inner tube is shaped like a dome at the end, and has a ⅛-inch tube (with a thickness of 0.2 mm to 0.5 mm) extended at the center.

The liquid catch plate, when the dual concentric tube-type nozzle is employed, may have any shape without particular limitation, and preferably has a shape of short column, on the circular face of which the analysis liquid may be caught. In a preferred case, the circular face of the liquid catch plate, on which the analysis liquid is caught, is properly processed in advance to have a diameter matched to the diameter of the nozzle body of the dual concentric tube-type nozzle. For example, for a dual concentric tube-type nozzle with a 10-mm inner tube (8 mm in inner diameter, 12 mm in outer diameter), a 20-mm outer tube (18 mm in inner diameter, 22 mm in outer diameter), and a ⅛-inch tube, the circular face of the liquid catch plate, on which the analysis liquid is caught, may have a diameter of 8 to 12 mm.

Advantageous Effects of the Invention

As has been explained above, the present invention enables speedy analysis of the end part of the substrate such as semiconductor wafer, by use of an apparatus with more simple structure. More specifically, the present invention enables speedy analysis of only within the bevel part or over the edge part of the substrate.

DESCRIPTION OF EMBODIMENT

Figure 2:
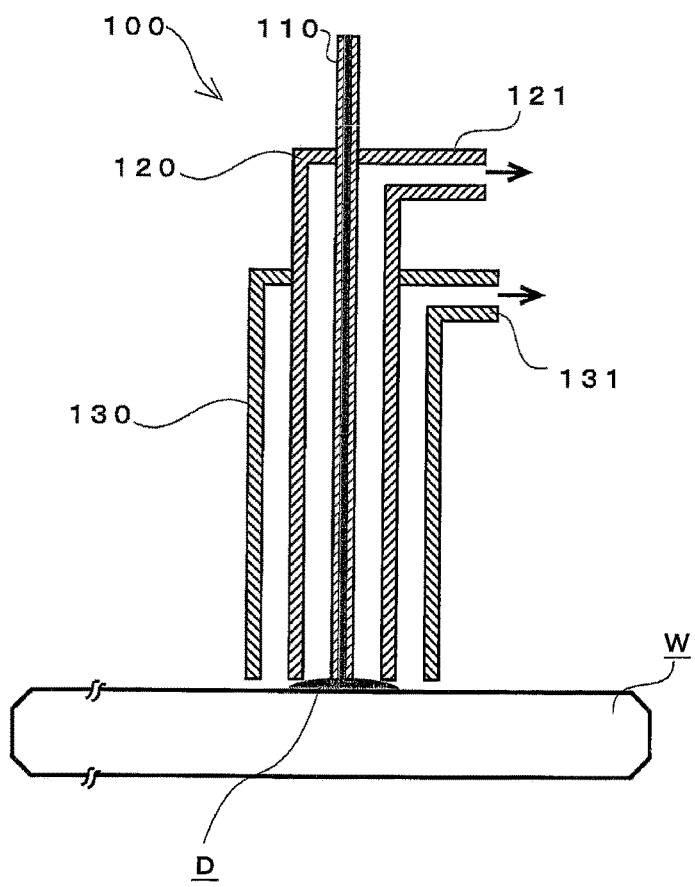
FIG. 2 is a schematic cross-sectional view that illustrates a substrate analyzer of this embodiment.

Embodiments of the present invention will be explained below. FIG. 2 shows a schematic cross-sectional view that illustrates a substrate analyzer of this embodiment.

A nozzle 100 illustrated in FIG. 2 is constituted by a triple concentric tube that includes an inner tube 110, a first outer tube 120 arranged around an outer circumference of the inner tube 110, and a second outer tube 130 arranged around an outer circumference of the first outer tube 120. The inner tube 110 has a syringe pump (not illustrated) connected thereto, enabling suction and discharge of an analysis liquid through the inner tube 110.

The first outer tube 120 has arranged thereto a first exhaust unit 121 which is connected to an evacuation pump (not illustrated), making it possible to keep a space (first exhaust path) formed between the inner tube 110 and the first outer tube 120 under a depressurized atmosphere. Similarly, a second exhaust unit 131, to which an evacuation pump (not illustrated) is connected, is arranged between the first outer tube 120 and the second outer tube 130, making it possible to keep a space (second exhaust path) formed between the first outer tube 120 and the second outer tube 130 under a depressurized atmosphere.

A substrate analyzer of this embodiment can analyze a substrate surface, according to the procedures below. The nozzle 100 is lowered toward a substrate W to an extent that the tip is not brought into contact with the substrate surface, and the analysis liquid is discharged through the inner tube 110. While this state is kept, the substrate surface is scanned with the analysis liquid. The nozzle is then stopped after completion of a predetermined scanning operation, the analysis liquid is sucked up through the inner tube 110, and collected into the syringe pump. The collected analysis liquid is analyzed by use of an analyzer such as ICP-MS.

Figure 3:
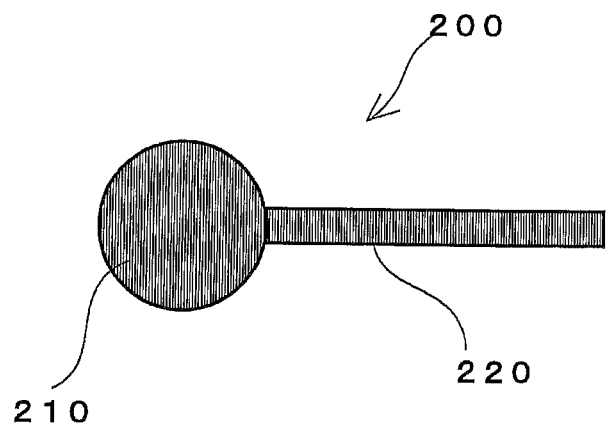
FIG. 3 is a plan view that illustrates a liquid catch plate.

Next, a case where the end part of the substrate is analyzed by use of the substrate analyzer of this embodiment will be explained. FIG. 3 is a plan view that illustrates a liquid catch plate 200. The liquid catch plate 200 is formed of PTFE, and has a circular plate 210 for catching an analysis liquid D, and a shaft 220 which is attached to the circular plate 210. When employing a triple concentric tube-type nozzle with a 20-mm second outer tube (18 mm in inner diameter, 22 mm in outer diameter), a 10-mm first outer tube (8 mm in inner diameter, 12 mm in outer diameter), and a ⅛-inch tube, then the diameter of the circular face 210 of the liquid catch plate 200 was set to 12 mm.

Figure 4:
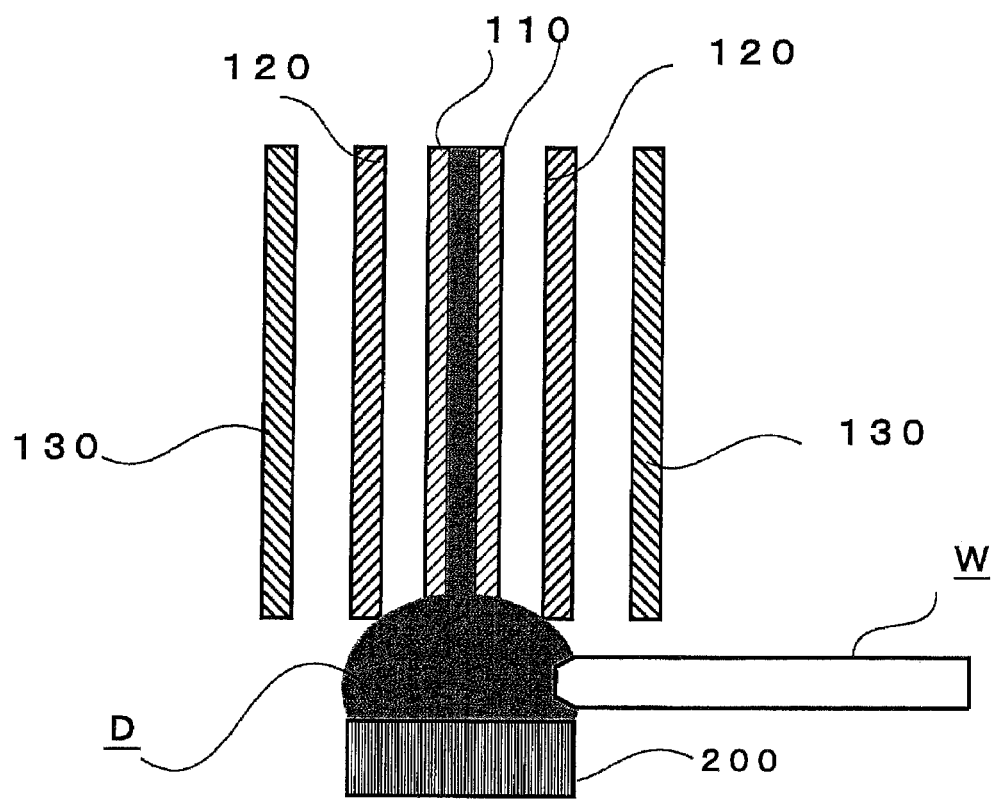
FIG. 4 is a schematic cross-sectional view that illustrates a mode of analysis of the end part of the substrate.
Figure 5:
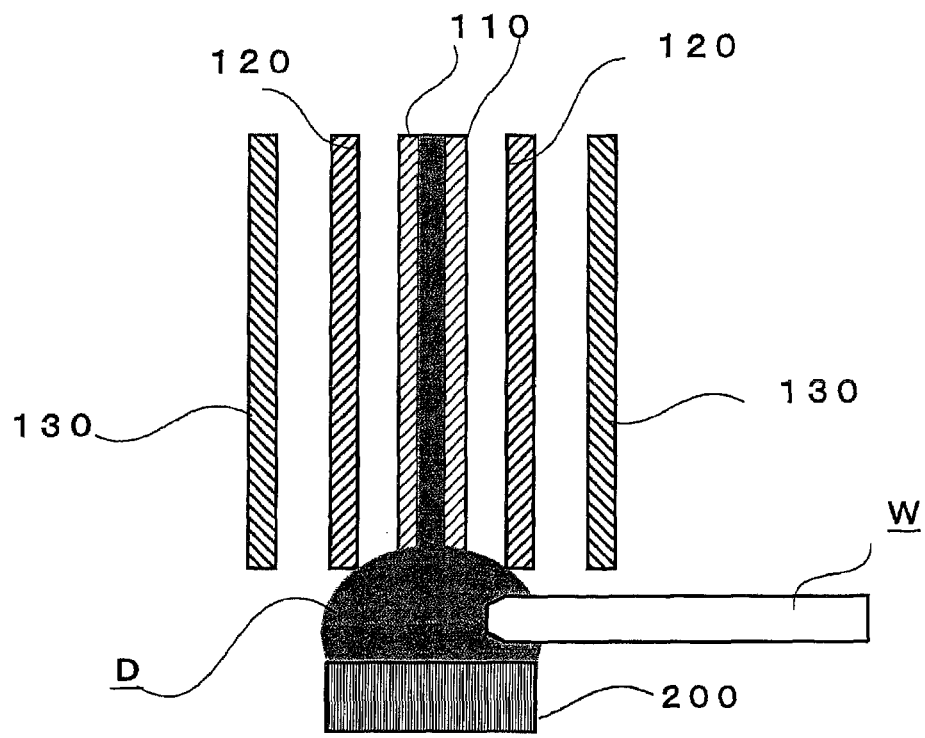
FIG. 5 is a schematic cross-sectional view that illustrates a mode of analysis of the end part of the substrate.

FIGS. 4 and 5 are schematic cross-sectional views that illustrate modes of analysis of the end part of the substrate. When the end part of the substrate is analyzed, the circular face 210 of the liquid catch plate 200 is first arranged below and in proximity to the nozzle tip. In this state, the analysis liquid is discharged through the inner tube 110. In this process, the first exhaust path and the second exhaust path are kept under a depressurized atmosphere. The analysis liquid D discharged through the inner tube 110 is controlled to be caught over the entire range of the circular face 210 of the liquid catch plate 200. The analysis liquid D discharged through the inner tube 110 then becomes retained between the nozzle tip and the liquid catch plate, by the action of surface tension and the depressurized atmosphere in the first exhaust path and the second exhaust path.

Figure 1:
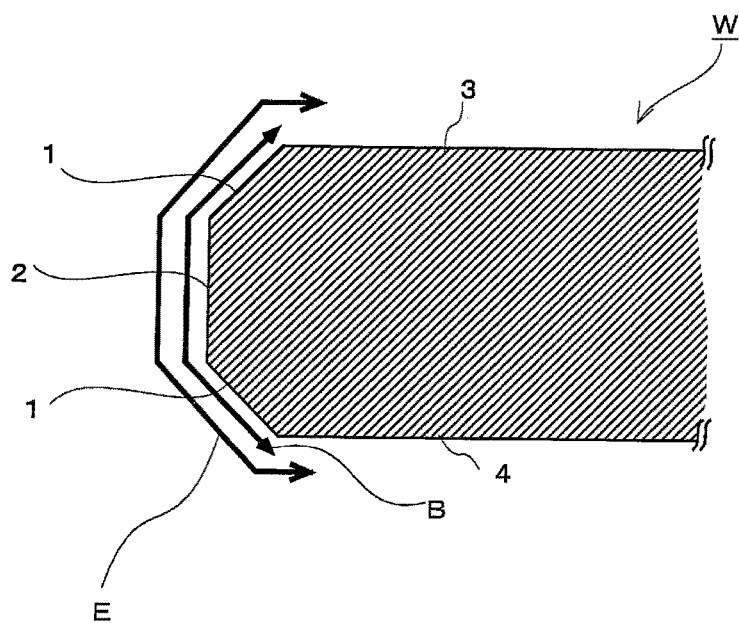
FIG. 1 is a cross-sectional view that illustrates an end part of a substrate.

After the analysis liquid D is thus kept retained, the substrate W is then moved so as to bring the end part thereof into contact with the analysis liquid D. While the contact state of the end part of the substrate W is controlled, the bevel part B illustrated in FIG. 1 is analyzed (FIG. 4), or the edge part E is analyzed (FIG. 5).

Measurement results of the end part of the substrate W will be explained. A 12-inch silicon wafer was employed as a substrate to be analyzed. The substrate has a thickness of 0.775 mm±0.02 mm, with the circumferential end part processed by so-called beveling (chamfering). The analysis liquid was a mixed solution of 3 vol % hydrogen fluoride and 4 vol % hydrogen peroxide solutions, and for use, 1 mL of which was sucked up in the ⅛-inch tube of the nozzle.

The nozzle tip and the liquid catch plate were set 2.5 mm away from each other, and 200 μL of the analysis liquid was discharged through the ⅛-inch tube of the nozzle so as to allow the analysis liquid to be retained between the nozzle tip and the liquid catch plate. Now, any change in the distance between the nozzle tip and the liquid catch plate will need suited control of the volume of discharge of the analysis liquid, in which for a distance of 2 to 3 mm, the volume of discharge is controlled within the range of 100 to 300 μL.

With the analysis liquid retained between the nozzle tip and the liquid catch plate, the end part of the substrate was moved to an intermediate position between the nozzle tip and the liquid catch plate, where the end part of the substrate was brought into contact with the analysis liquid. Operation for such contact of the end part may be monitored under a microscope (under magnification). Now in a case where the bevel part B illustrated in FIG. 1 is to be analyzed, the end part of the substrate was brought into contact with the analysis liquid as illustrated in FIG. 4. While the state is kept, the nozzle and the liquid catch plate were synchronously moved relative to the substrate (30 mm/min), along the outer circumference of the substrate. (Moved at 5 mm/min, for hydrophilic wafer). Also during movement, the contact state of the end part of the substrate and the analysis liquid was monitored under a microscope. After the relative movement over a part to be analyzed, the analysis liquid was sucked up, and analyzed by ICP-MS.

Table 1 summarizes results of ICP-MS analysis, with a volume of collected analysis liquid of 300 μL, obtained after scanning the edge part of the 12-inch silicon wafer (with a total scanned area of the edge part of 7.3 cm$^2$).

TABLE 1

| Elements | Mass number (g) | Concentration in collected liquid (ppt) | Concentration (atoms/cm$^2$) |
|---|---|---|---|
| Na | 22.98977 | 5 | 5.38E+09 |
| Mg | 24.305 | 1.2 | 1.22E+09 |
| Al | 26.9815386 | 8 | 7.34E+09 |
| K | 39.0983 | 4 | 2.53E+09 |
| Ca | 40.078 | 6 | 3.70E+09 |
| Cr | 51.9961 | 5 | 2.38E+09 |
| Mn | 54.938045 | 0.7 | 3.15E+08 |
| Fe | 55.845 | 2 | 8.86E+08 |
| Co | 58.933195 | 0.2 | 8.40E+07 |
| Ni | 58.6934 | 1.3 | 5.48E+08 |
| Cu | 63.546 | 1 | 3.89E+08 |
| Zn | 65.409 | 3 | 1.13E+09 |

TABLE 1-continued

| Elements | Mass number (g) | Concentration in collected liquid (ppt) | Concentration (atoms/cm$^2$) |
|---|---|---|---|
| Zr | 91.224 | 0.14 | 3.80E+07 |
| Mo | 95.94 | 0.8 | 2.06E+08 |
| Sn | 118.71 | 2 | 4.17E+08 |
| Sb | 121.76 | 1.43 | 2.91E+08 |
| W | 183.84 | 0.3 | 4.04E+07 |
| Pb | 207.2 | 0.1 | 1.19E+07 |

It was revealed from the analytical results of the end part of the substrate summarized in Table 1 that metal pollution only in the edge part of wafer can be easily analyzed.

This embodiment, although having exemplified above a case of silicon wafer, is applicable to various types of substrate with different materials and sizes. This embodiment is also applicable to both of hydrophobic and hydrophilic substrates. The analysis liquid can employ various types of solution other than the mixed solution of hydrogen fluoride and hydrogen peroxide, which include aqua regia-based solution (for precious metals to be analyzed) and nitric acid solution (for hydrophilic substrate to be analyzed).

REFERENCE SIGNS LIST

1 Chamfered part
2 Outermost edge
100 Nozzle
110 Inner Tube
120 First outer tube
130 Second outer tube
B Bevel part
E Edge part
W Wafer
D Analysis liquid

The invention claimed is:
1. An analysis method of a substrate by use of a nozzle for substrate analysis, which discharges an analysis liquid from a tip of the nozzle, scans a surface of the substrate with a discharged analysis liquid, and then sucks the analysis liquid, comprising the steps of:
arranging, opposite to a nozzle tip, a liquid catch plate that catches the discharged analysis liquid, to thereby retain the analysis liquid discharged from the tip between the nozzle tip and the liquid catch plate;
positioning the substrate so that an end part thereof can be inserted between the nozzle tip and the liquid catch plate;
bringing the end part of the substrate into contact with the analysis liquid retained between the nozzle tip and the liquid catch plate; and
moving the nozzle and the liquid catch plate concurrently along a periphery of the substrate, while keeping the end part of the substrate in contact with the analysis liquid, to thereby analyze the end part of the substrate,
wherein the nozzle is constituted by a triple concentric tube that includes an inner tube through which the analysis liquid is discharged and sucked; a first outer tube arranged around an outer circumference of the inner tube so as to surround the analysis liquid dragged for scanning; and a second outer tube arranged around an outer circumference of the first outer tube, and the nozzle further includes a first exhaust unit having an exhaust path arranged between the inner tube and the first outer tube; and a second exhaust unit having an exhaust path arranged between the first outer tube and the second outer tube.

2. A substrate analyzer comprising:
a nozzle for substrate analysis which discharges an analysis liquid from a tip of the nozzle, scans a substrate surface with a discharged analysis liquid, and then sucks the analysis liquid, said nozzle for substrate analysis constituted by a triple concentric tube that includes an inner tube through which the analysis liquid is discharged and sucked; a first outer tube arranged around an outer circumference of the inner tube so as to surround the analysis liquid dragged for scanning; and a second outer tube arranged around an outer circumference of the first outer tube, wherein the nozzle further includes a first exhaust unit having an exhaust path arranged between the inner tube and the first outer tube; and a second exhaust unit having an exhaust path arranged between the first outer tube and the second outer tube;
a liquid catch plate control unit that arranges, opposite to the nozzle tip, a liquid catch plate that catches the analysis liquid discharged through the inner tube; and
a drive unit capable of synchronously moving the nozzle and the liquid catch plate relative to the substrate.

3. An analysis method of a substrate by use of a nozzle for substrate analysis, which discharges an analysis liquid from a tip of the nozzle, scans a surface of the substrate with a discharged analysis liquid, and then sucks the analysis liquid, comprising the steps of:
arranging, opposite to a nozzle tip, a liquid catch plate that catches the discharged analysis liquid, to thereby retain the analysis liquid discharged from the tip between the nozzle tip and the liquid catch plate;
positioning the substrate so that an end part thereof can be inserted between the nozzle tip and the liquid catch plate;
bringing the end part of the substrate into contact with the analysis liquid retained between the nozzle tip and the liquid catch plate; and
moving the nozzle and the liquid catch plate concurrently along a periphery of the substrate, while keeping the end part of the substrate in contact with the analysis liquid, to thereby analyze the end part of the substrate, wherein the liquid catch plate is hydrophobic, and wherein the nozzle is constituted by a triple concentric tube that includes an inner tube through which the analysis liquid is discharged and sucked; a first outer tube arranged around an outer circumference of the inner tube so as to surround the analysis liquid dragged for scanning; and a second outer tube arranged around an outer circumference of the first outer tube, and the nozzle further includes a first exhaust unit having an exhaust path arranged between the inner tube and the first outer tube; and a second exhaust unit having an exhaust path arranged between the first outer tube and the second outer tube.

* * * * *